United States Patent [19]

Kawamura et al.

[11] 4,054,499
[45] Oct. 18, 1977

[54] PROCESS FOR PRODUCING 2-CHLOROPYRIDINE

[75] Inventors: Masao Kawamura, Akashi; Tadaaki Nishi; Hiro Tsuchiya, both of Kakogawa; Syuzi Takagi, Akashi, all of Japan

[73] Assignee: Seitetsu Kagaku Co., Ltd., Japan

[21] Appl. No.: 663,890

[22] Filed: Mar. 4, 1976

Related U.S. Application Data

[63] Continuation of Ser. No. 530,478, Dec. 6, 1974, abandoned.

[51] Int. Cl.² ............................................. B01J 1/10
[52] U.S. Cl. ........................................... 204/158 HA
[58] Field of Search .............................. 204/158 HA

[56] References Cited

U.S. PATENT DOCUMENTS 3,297,556  1/1967  Boudakian et al. .......... 204/158 HA

Primary Examiner—Howard S. Williams
Attorney, Agent, or Firm—Pollock, Vande Sande & Priddy

[57] ABSTRACT

Pyridine is reacted with chlorine at a molar ratio of pyridine to chlorine of 0.5–10 : 1 in a gaseous phase in the presence of at least 0.2 moles, preferably 1 to 20 moles of steam per mole of pyridine under irradiation of ultraviolet rays of 2000–5000 A, thereby producing 2-chloropyridine.

7 Claims, No Drawings

PROCESS FOR PRODUCING 2-CHLOROPYRIDINE

This is a continuation of application Ser. No. 530,478 filed Dec. 6, 1974, and now abandoned.

This invention relates to an improvement in a process for producing 2-chloropyridine from pyridine and chlorine, using photolytic light.

2-Chloropyridine is useful as raw materials for agricultural chemicals, pharmaceutical chemicals and other industrial chemicals.

Heretofore, several processes have been proposed for producing 2-chloropyridine from pyridine and chlorine, and these processes can be classified into two major groups, that is, processes for carrying out thermal reaction at an elevated temperature and processes for carrying out photolytic reaction under irradiation of ultraviolet rays.

Examples of the former thermal reaction are disclosed in U.S. Pat. Nos. 2,820,791 and 3,153,044 where pyridine reacts with chlorine in the presence of water or carbon tetrachloride as a diluent at an elevated temperature such as 260° to 420° C. Thus, not only selection of corrosion-resistant materials of construction is an important problem in the practice of the processes in an industrial scale, but also hardly separable or removably by-products and 20 to 50% of tarry matters are inevitably contained in the resulting reaction products, and cause clogging of reactor or conduits, rendering continuation of the reaction difficult. Furthermore, a risk of explosion cannot be completely eliminated in the reaction at the elevated temperature, even if a diluent is used.

On the other hand, an example of the latter process for photolytic reaction is disclosed in U.S. Pat. No. 3,297,556, where pyridine reacts with chlorine in a liquid or gaseous phase under irradiation of light to produce 2-chloropyridine. In the photolytic process, the reaction temperature is so low that improvements are made as to the difficulty in selecting materials of construction and the risk of explosion. However, when the photolytic process is carried out in a liquid phase, halogenated hydrocarbons or a mixture of excess pyridine with water is used as a diluent, and the reaction is carried out at a boiling temperature, but the yield is not satisfactory and a considerably large amount of the diluent must be used, as compared with the amount of the reactants, rendering a 2-chloropyridine concentration of the product mixture lower, for example, 2%. Thus, an enormous amount of the product mixture must be concentrated in purifying 2-chloropyridine. Even if halogenated hydrocarbons are used as a diluent, tar formation is liable to take place unless there is water, and the formed tarry matters attach to a surface of light irradiation source and inhibit light transmission. However, according to experiments conducted by the present inventors, reaction of chlorine with water to form hydrochloric acid takes place in preferance to formation of 2-chloropyridine, and 2-chloropyridine is hardly formed, when the reaction is carried out in a liquid phase, using only water as the diluent.

In said U.S. Pat. No. 3,297,556, it is disclosed that said photolytic reaction is carried out in a gaseous phase, using carbon tetrachloride as a diluent. However, according to the experiments conducted by the present inventors, considerable amounts of tarry matters and other by-products attached to wall surface of reactor tube in said gaseous phase photolytic process, rendering light transmission difficult and causing clogging of a conduit for withdrawing the product mixture. Thus, it is hard to continue the reaction.

An object of the present invention is to provide an improved process for producing 2-chloropyridine in high yield free from any risk of explosion by carrying out photolytic reaction of pyridine with chlorine in a vapor phase under irradiation of ultraviolet rays.

Another object of the present invention is to provide an excellent photolytic process completely free from any trouble of inhibition of light transmission or conduit clogging caused by attachment of tarry matters and other by-products by suppressing tar and by-product formation side-reaction.

Other object of the present invention is to provide a process for continuously producing 2-chloropyridine readily in an industrial scale.

As a result of extensive studies on eliminating said disadvantages of the prior art processes and attaining said objects, the present inventors have found that photolytic reaction of pyridine with chlorine can be carried out in high yield with high selectivity without any risk of explosion if a mixture of pyridine with chlorine is subjected to the reaction in a gaseous phase in the presence of at least 0.2 moles, preferably 1 to 20 moles of steam per one mole of pyridine. The effect appears in the presence of at least 0.2 moles of steam. Though details of actions attained in the present invention have not been completely clarified yet, it seems that by-produced hydrochlorides, etc. attaching to wall surfaces of reactor absorb steam of reaction system to form an aqueous hydrochloride solution and wet the wall surfaces of reactor. The resulting aqueous hydrochloride solution is readily discharged to the outside of the reactor together with the reaction gas mixture, keeping the wall surfaces of reactor always clear and continuing the reaction without any trouble.

That is to say, the gist of the present invention resides in an improved process for producing 2chloropyridine, where 2-chloropyridine is produced by reaction of pyridine with chlorine in a gaseous phase under irradiation of photolytic light, characterized by carrying out the reaction in the presence of steam.

In the present invention, pyridine and chlorine are used in the well known molar ratio, that is, a molar ratio of pyridine to chlorine of 0.5–10: 1, preferably 1.5–5:1, more preferably 2–3:1.

when steam is used in the present invention, it is effective to use at least 0.2 moles of steam per one mole of pyridine, but usually 1 to 20, preferably about 2 to 15 moles of steam is used per one mole of pyridine. If the amount of steam is too small, the reaction temperature is excessively elevated, and the amount of by-produced pyridine hydrochloride is increased thereby. The by-produced pyridine hydrochloride deposits on wall surfaces of reactor, and the effect of steam addition is hardly expectable. If the amount of steam is too large, the concentration of 2-chloropyridine in the resulting reaction product mixture is lowered, and purification and separation of 2-chloropyridine will be difficult to carry out, though the excessive steam will not inhibit the reaction.

Water can be added to the reaction system in any manner. For example, water and raw materials are separately vaporized, and then led to a reactor, or water is led to a reactor by making water flow down along an inner wall of a reactor, and vaporizing the water while the water flows down. However, it is preferable to mix water with the raw material pyridine at said mixing ratio, pass the resulting mixture through an appropriate vaporizer, thereby vaporizing the mixture, lead the resulting gaseous mixture of pyridine and steam to a reactor and react the pyridine with chlorine gas therein.

According to the present invention, a mixture of pyridine and steam, and chlorine are continuously charged in a gaseous phase into a reactor and subjected to photolytic reaction under irradiation of ultraviolet rays of 2,000 to 5,000 A from an outside or inside light source. It is desirable to feed the mixture of pyridine and water and chlorine to the reactor at a temperature as low as possible which permits them to be kept in a gaseous state, because the reaction is an exothermic one. In the present invention, it is more efficient and convenient to use a reactor provided with a light source of inside irradiation type.

The resulting product mixture is totally condensed by a cooler connected to the outlet of reactor, and then the condensate can be readily purified according to the well known procedures, for example, by a combination of neutralization, extractive separation and distillation, as disclosed in U.S. Pat. Nos. 2,820,791 and 3,153,044. The present process is easily practicable in continuous manner and suitable for industrial scale operation.

Now, the present invention will be hereunder described in detail, referring to examples, but the present invention is not limited to these examples.

EXAMPLE 1

A light source-cooling pipe was placed at a center of a cylindrical glass reactor with a jacket (reactor capacity: 2.5 l; outer diameter: 140 mm; inner diameter: 120 mm; length : 230 mm) provided with a chlorine feeding pipe, a pyridine-water mixture vaporizer, a thermometer, etc., and a light source was fixed approximately at the center of the reactor. Separately, a four-necked flask having a capacity of 1 l, provided with a cooler was disposed just under the reactor as a receiver, and uncondensed gas was made to be passed through a cooler and absorbed in an aqueous alkali solution.

The inside temperature of the reactor was elevated to 130° C by circulating oil through the jacket part of the reactor and an oil bath provided separately. Then, a pyridine-water mixture (molar ratio = 1 : 4) was passed through the vaporizer and led to the reactor. Then, the light source (high pressure mercury lamp, 100 W, type UM-102, made by Ushio Denki K.K., Japan) was turned on. Successively, chlorine gas was led to the reactor, and subjected to reaction. Inside temperature of the reactor was elevated to 160° C. The reaction was carried out for 20 minutes, and there was no deposition of tarry matters on wall surfaces of the reactor and light source-cooling pipe. That is, the reaction proceeded smoothly. In that reaction, 194 g of pyridine, 176 g of water and 86.5 g of chlorine were used.

After the completion of reaction, the reaction product liquid within the receiver was separated into two layers, and 94.4 g of 2-chloropyridine, 13.3 g of 2,6-dichloropyridine and 112 g of unreacted pyridine were contained in these two layers, but no unreacted chlorine was observed therein.

Yield of 2-chloropyridine in that reaction was 33.9% by mole on the basis of the fed pyridine.

Examples 2-5

Reaction was carried out in the same manner as in Example 1, using the same reactor apparatus as used in Example 1, but changing molar ratios of pyridine-water-chlorine as shown in Table. Results of analysis of the reaction products are given in Table.

| Example No. | Amount charged (g) | | | Molar Ratio | | | Formed 2-chloro-pyridine (g) | Formed 2,6-di-chloro-pyridine (g) | Reacted pyridine (g) | Yield (% by mole) | |
|---|---|---|---|---|---|---|---|---|---|---|---|
| | Pyri-dine | Water | Chlo-rine | Pyri-dine | Water | Chlo-rine | | | | Based on reacted pyridine | Based on fed pyridine |
| 2 | 269 | 643 | 123 | 2.0 | 20.7 | 1.0 | 125 | 15.8 | 121 | 71.4 | 32.3 |
| 3 | 470 | 536 | 208 | 2.0 | 10.2 | 1.0 | 200 | 40.1 | 167 | 83.0 | 29.6 |
| 4 | 572 | 434 | 212 | 2.4 | 8.1 | 1.0 | 190 | 18.6 | 143 | 92.3 | 23.1 |
| 5 | 642 | 366 | 212 | 2.7 | 6.8 | 1.0 | 160 | 5.80 | 115 | 96.6 | 17.3 |

What is claimed is:

1. A process for producing 2-chloropyridine by reaction of pyridine with chlorine in a molar ratio of pyridine to chlorine of 0.5:1 - 10:1 under irradiation of photolytic light of 2,000 to 5,000 A in the gaseous phase, which comprises:
   A. feeding and evaporating pyridine to provide gaseous pyridine in a reactor having therein a light source lamp means provided with a light source cooling means;
   B. feeding and evaporating 2 to 15 moles of water per mole of pyridine to provide steam in said reactor;
   C. feeding chlorine to said reactor; and
   D. providing photolytic light of 2,000 to 5,000 A from said light source lamp to thereby effect photolytic reaction in the gaseous phase to provide said 2-chloropyridine, and wherein said light source lamp is cooled by means of said light source cooling means.

2. A process according to claim 1 wherein 1.5 to 5 moles of pyridine are used per mole of chlorine.

3. A process according to claim 1 wherein the pyridine and the water are mixed together, evaporated and then fed to the reactor.

4. A process according to claim 1 wherein the reaction is carried out by supplying water to inner wall of the reactor and surface of the light source lamp.

5. A process according to claim 1 wherein a light source lamp provided with a light source cooler is disposed in the reactor provided with a cooling jacket, the reaction is maintained at first at about 130° C, then a mixture of pyridine and water is vaporized and fed to the reactor, then a chlorine gas is passed through the reactor while maintaining the reactor at about 160° C, thereby carrying out the photolytic reaction.

6. The process of claim 1 wherein 2 to 3 moles of pyridine are used per mole of chlorine.

7. The process of claim 1 wherein the temperature in said reactor is maintained as low as possible while permitting reactants to be kept in a gaseous state.

* * * * *